United States Patent [19]
Rutsch et al.

[11] Patent Number: 5,210,110
[45] Date of Patent: May 11, 1993

[54] SILYLATED ACYLPHOSPHINE OXIDES

[75] Inventors: Werner Rutsch, Fribourg; Rinaldo Hüsler, Wünnewil, both of Switzerland

[73] Assignee: Ciba-Geigy Corporation, Ardsley, N.Y.

[21] Appl. No.: 793,759

[22] Filed: Nov. 18, 1991

[30] Foreign Application Priority Data

Nov. 21, 1990 [CH] Switzerland ............... 3689/90-0

[51] Int. Cl.⁵ ............... C08F 2/50; C07F 9/02; C07F 9/06; C07D 330/00
[52] U.S. Cl. ............... 522/64; 546/14; 546/22; 549/6; 549/218; 556/405; 558/178; 568/15
[58] Field of Search ............... 522/64; 546/14, 22; 549/6, 218; 556/405; 558/178; 568/15

[56] References Cited

U.S. PATENT DOCUMENTS

| | | | |
|---|---|---|---|
| 4,298,738 | 11/1981 | Lechtken et al. | 546/22 |
| 4,512,924 | 4/1985 | Attwood et al. | 260/243.3 |
| 4,658,024 | 4/1987 | Attwood et al. | 540/500 |
| 4,710,523 | 12/1987 | Lechtken et al. | 522/14 |
| 4,747,593 | 5/1988 | Stobb | 271/213 |
| 4,772,701 | 9/1988 | Attwood et al. | 544/235 |
| 4,792,632 | 12/1988 | Ellrich et al. | 568/15 |
| 4,808,713 | 2/1989 | Attwood et al. | 540/487 |

OTHER PUBLICATIONS

Chem. Abst. 68, 87343q.
Chem. Abst. 93, 132614l (1980).
Chem. Abst. 79, 5402y (1973).
W. Adam et al., J. Org. Chem. (1980) 4167.
Chem. Abst. 78, 43609h (1973).
Chem. Abst. 78, 57505h (1973).
Chem. Abst. 80, 59044x (1974).
Chem. Abst. 78, 83559y (1973).
Chem. Abst. 75, 87729q (1971).
Chem. Abst. 78, 136372r (1973).
Chem. Abst. 69, 27522h (1968).
Chem. Abst. 72, 90571a (1970).
Chem. Abst. 70, 4193h (1969).
E. Kuyl-Yeheskiely et al., Rec. Trav. Chim. Pays & Bas 105, 505 (1986).
J. Zygmunt et al., Synthesis (1978), 609.
M. Sekine et al., J. Chem. Soc. Chem. Comm. 1978, 285.
G. M. Blackburn et al., Chem. Soc. Chem. Comm. 1978, 870.
A Kline, et al., J. Org. Chem. 49, 21-39-42.
C. E. McKenna et al., Tetrahedron Letters 2, 155-8 (1977).
T. Morita et al., Tetrahedron Letters 28, 2523-6 (1978).
Y. Morita, et al., Bull Chem. Soc. Jp. 51, 2169 (1978).
R. Rabinowitz, J. Org. Chem. 28, 2975 (1963).
C. E. McKenna et al., J.C.S. Chem. Comm. (1979) 739.
Houken-Weyl, vol. XII/1, 324 (1963).

*Primary Examiner*—Cynthia Hamilton
*Assistant Examiner*—Susan Berman
*Attorney, Agent, or Firm*—Luther A. R. Hall; William A. Teoli, Jr.

[57] ABSTRACT

Silylated acylphosphine oxides of formula I

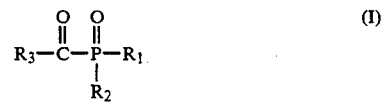

in which $R_1$, $R_2$ and $R_3$ are defined in the specification, are highly suitable as photoinitiators for the photopolymerization of compounds which can be polymerized by means of free radicals, namely ethylenically unsaturated compounds.

15 Claims, No Drawings

SILYLATED ACYLPHOSPHINE OXIDES

The invention relates to photocurable compositions which contain silylated acylphosphine oxides, to the use of silylated acylphosphine oxides as photoinitiators for the photopolymerisation of compounds containing ethylenically unsaturated double bonds, to a process for the photopolymerisation of such compounds using silylated acylphosphines as photoinitiators, and to novel silylated acylphosphine oxides.

EP-B-7 508 and EP-A-42 567 disclose unsilylated monoacylphosphine oxides as photoinitiators. EP-A-184 095 uses bisacylphosphine oxides as photoinitiators. The syntheses and spectroscopic analyses of some silylated acylphosphine oxides have also already been described in the literature. For example, corresponding bis(trimethylsilyl) esters are disclosed in Chemical Abstracts 93(13):132614h; Chemical Abstracts 79(1):5402y and J. Org. Chem. 45(21), 4162-7, 1980. Bis(triethylsilyl) esters are disclosed in Chemical Abstracts 78(7):43609h; Chemical Abstracts 78(9):57505h; Chemical Abstracts 80(11):59044x; Chemical Abstracts 78(13):83559y; Chemical Abstracts 75(13):87729q and Chemical Abstracts 78(21):136372r. Corresponding monosilyl esters are disclosed in SU-193 505. Compounds containing two different silyl ester radicals are disclosed in Chemical Abstracts 72(17):90571a and Chemical Abstracts 70(1):4193h. In particular, the silylated acylphosphine oxides are known as intermediates in the preparation of phosphonic acids and nucleosidic phosphonates. Thus, they are described as intermediates, for example, in Rec. Trav. Chim. Pays-Bas 105(11),505-6,1986; Synthesis (8),609-12,1978; J. Chem. Soc., Chem. Comm.(7),285-6,1978; J. Chem. Soc., Chem. Comm.(20),870-1,1978; J. Chem. Soc., Chem. Comm. (17),739,1979; J. Org. Chem. 49(12),2139-43,1984; THL (2),155-8,1977; THL (28),2523-6,1978 and Bull. Chem. Soc. Jp. 51(7),2160-70,1978.

It has now been found that silylated acylphosphine oxides are highly suitable as photoinitiators for the polymerisation of compounds containing ethylenically unsaturated double bonds.

The invention thus relates to photopolymerisable compositions comprising
(a) at least one ethylenically unsaturated, photopolymerisable compound and
(b) as photoinitiator at least one compound of the formula I

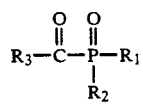
(I)

in which
$R_1$ is the

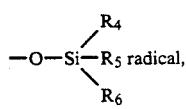
radical, $R_2$ is as defined for $R_1$, it being possible for $R_1$ and $R_2$ as

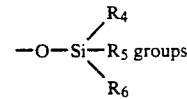
groups to be identical or different, or $R_2$ is $C_1$–$C_{18}$alkyl, phenyl-, $C_1$–$C_{12}$alkoxy- or halogen-substituted $C_1$–$C_8$alkyl, $C_2$–$C_{18}$alkenyl, unsubstituted or $C_1$–$C_{12}$alkyl-, $C_1$–$C_{12}$alkoxy-, phenyl- or halogen-substituted $C_5$–$C_8$cycloalkyl, unsubstituted or halogen-, $C_1$–$C_{12}$alkyl- or $C_1$–$C_{12}$alkoxy-substituted $C_6$–$C_{12}$aryl, an aromatic, O-, S- and/or N-containing 5- or 6-membered heterocyclic radical, which may be substituted by halogen, $C_1$–$C_4$alkyl or $C_1$–$C_4$alkoxy, or is $C_1$–$C_{12}$alkoxy, phenoxy or benzyloxy, and, if $R_2$ is a

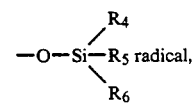
radical, $R_6$ can link the silicon atoms to form 6-, 7- or 8-membered rings, in which case

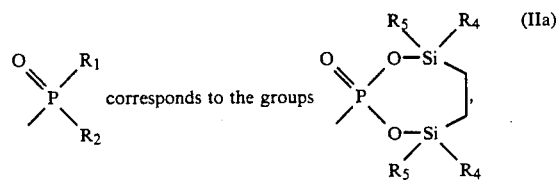

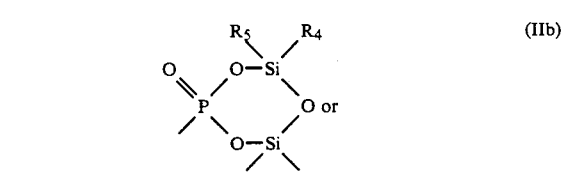

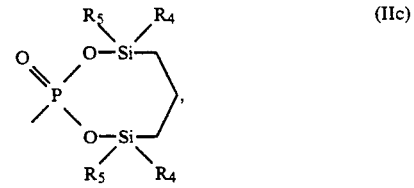

or $R_1$ and $R_2$, together with the —P=O group, can form a 4-membered ring of the formula

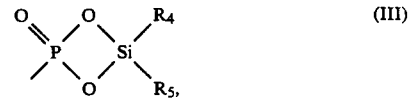
(III)

$R_3$ is $C_1$–$C_{18}$alkyl, halogen-, phenyl- or $C_1$–$C_{12}$alkoxy-substituted $C_1$–$C_8$alkyl, $C_2$–$C_6$alkenyl, unsubstituted or $C_1$–$C_{12}$alkyl-, $C_1$–$C_{12}$alkoxy- or halogen-substituted $C_5$–$C_8$cycloalkyl, unsubstituted or $C_1$–$C_{12}$alkyl-, $C_1$–$C_{12}$alkoxy-, $C_2$–$C_{12}$alkoxyalkyl-, $C_1$–$C_4$alkylthio- or halogen-substituted $C_6$–$C_{12}$aryl, or a 5- or 6-membered, aromatic, O-, S- and/or N-containing heterocyclic radical, which may be substituted by halogen, $C_1$–$C_4$alkyl or $C_1$–$C_4$alkoxy, and $R_4$, $R_5$ and $R_6$, independently of one another, are hydrogen, $C_1$–$C_{18}$alkyl, $C_5$–$C_8$cycloalkyl, $C_1$–$C_{12}$alkoxy or unsubstituted or $C_1$–$C_8$alkyl-substituted phenyl, at least two of the radicals $R_4$, $R_5$ and $R_6$ being other than hydrogen.

$C_1$–$C_{18}$Alkyl $R_2$, $R_3$, $R_4$, $R_5$ and $R_6$ may be branched or unbranched, for example methyl, ethyl, propyl, isopropyl, n-butyl, sec-butyl, tert-butyl, pentyl, hexyl, tert-hexyl, heptyl, octyl, nonyl, decyl, dodecyl, tetradecyl, heptadecyl or octadecyl. In particular, $R_2$, $R_3$, $R_4$, $R_5$ and $R_6$ are $C_1$–$C_{12}$alkyl.

Monosubstituted or polysubstituted, for example monosubstituted to trisubstituted, in particular monosubstituted or disubstituted, $C_1$–$C_8$alkyl $R_2$ and $R_3$ may be, for example, benzyl, 1-phenylethyl, 2-phenylethyl, α,α-dimethylbenzyl, 2-methoxyethyl, 2-ethoxyethyl, 2-butoxyethyl, 2-isopropoxyethyl, 2-butoxypropyl, 2-oxtyloxyethyl, chloromethyl, 2-chloroethyl or trichloromethyl, preferably benzyl.

$C_2$–$C_{18}$Alkenyl $R_2$ may be, for example, allyl, methallyl, 1,1-dimethylallyl, butenyl, 2-hexenyl, octenyl, undecenyl, dodecenyl or octadecenyl.

$C_2$–$C_6$Alkenyl $R_3$ may be, for example, vinyl, propenyl or butenyl.

$C_5$–$C_8$Cycloalkyl $R_2$ and $R_3$ may be, for example, cyclopentyl, cyclohexyl or cyclooctyl. Substituted, for example monosubstituted to tetrasubstituted, $C_5$–$C_8$cycloalkyl $R_2$ and $R_3$ may be, for example, methylcyclopentyl, dimethylcyclopentyl, methylcyclohexyl, dimethylcyclohexyl, diethylcyclohexyl, methoxycyclohexyl, dimethoxycyclohexyl, diethoxycyclohexyl, phenylcyclopentyl, phenylcyclohexyl, chlorocyclohexyl, dichlorocyclohexyl or dichlorocyclopentyl. $C_6$–$C_{12}$Aryl $R_2$ and $R_3$ may be, for example, phenyl, α-naphthyl, β-naphthyl or 4-diphenylyl, preferably phenyl. Substituted $C_6$–$C_{12}$aryl $R_2$ and $R_3$ preferably contain 1 to 3 substituents and are, for example, chlorophenyl, dichlorophenyl, trichlorophenyl, difluorophenyl, tolyl, mesityl, ethylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl or ethoxynaphthyl, in particular chlorophenyl or mesityl. Substituted aryl $R_3$ may additionally be, for example, methoxyethylphenyl, ethoxymethylphenyl, methylthiophenyl, isopropylthiophenyl or tert-butylthiophenyl. Alkyl and alkoxy as aryl substituents preferably have 1 to 4 carbon atoms and are, in particular, methyl or methoxy.

Heterocyclic $R_2$ and $R_3$ may be monocyclic or polycyclic, in particular monocyclic or dicyclic, for example containing a fused benzene ring, and are, for example, furyl, thienyl, pyrryl, pyridyl, indolyl, benzoxazolyl, benzimidazolyl or benzothiazolyl. A heterocyclic radical of this type preferably contains 4–12 carbon atoms. Said heterocyclic radicals may be monosubstituted or polysubstituted, for example monosubstituted or disubstituted. Examples are dimethylpyridyl, methylquinolyl, dimethylpyrryl, methoxyfuryl, dimethoxypyridyl and difluoropyridyl.

$C_1$–$C_{12}$Alkoxy $R_2$, $R_4$, $R_5$ and $R_6$ are, for example, methoxy, ethoxy, propoxy, butoxy or dodecoxy.

$C_1$–$C_8$Alkyl-substituted phenyl $R_4$, $R_5$ and $R_6$ preferably contain 1 to 3, in particular 1 or 2, alkyl substituents and are, for example, tolyl, xylyl, mesityl or ethylphenyl.

Halogen is preferably chlorine.

Preference is given to compositions in which $R_2$ is as defined for $R_1$, it being possible for $R_1$ and $R_2$ as

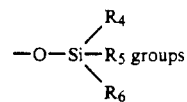

to be identical or different, or $R_2$ is $C_1$–$C_{12}$alkyl, phenyl-, $C_1$–$C_4$alkoxy- or halogen-substituted $C_1$–$C_8$alkyl, $C_2$–$C_8$alkenyl, unsubstituted or $C_1$–$C_4$alkyl-, $C_1$–$C_4$alkoxy-, phenyl- or halogen-substituted $C_5$–$C_8$cycloalkyl, unsubstituted or halogen-, $C_1$–$C_8$alkyl- or $C_1$–$C_4$alkoxy-substituted $C_6$–$C_{12}$aryl, or a 5- or 6-membered, aromatic, O-, S- and/or N-containing heterocyclic radical, which may be substituted by halogen, $C_1$–$C_4$alkyl or $C_1$–$C_4$alkoxy, or is $C_1$–$C_8$alkoxy, phenoxy or benzyloxy, and, if $R_2$ is a

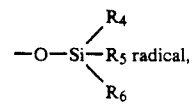

$R_6$ can link the silicon atoms to form 6-, 7- or 8-membered rings, in which case

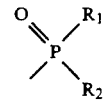

can correspond to the groups IIa, IIb or IIc, or $R_1$ and $R_2$, together with the —P═O group, can form a ring of the formula III, $R_3$ is $C_1$–$C_{12}$alkyl, halogen-, $C_1$–$C_4$alkoxy- or phenyl-substituted $C_1$–$C_8$alkyl, $C_2$–$C_4$alkenyl, unsubstituted or $C_1$–$C_8$alkyl-, $C_1$–$C_4$alkoxy-or halogen-substituted $C_5$–$C_8$cycloalkyl, unsubstituted or $C_1$–$C_8$alkyl-, $C_1$–$C_8$alkoxy-, $C_2$–$C_8$alkoxyalkyl-, $C_1$–$C_4$alkylthio- or halogen-substituted $C_6$–$C_{12}$aryl, or a 5- or 6-membered, aromatic, O-, S- and/or N-containing heterocyclic radical, which may be substituted by halogen, $C_1$–$C_4$alkyl or $C_1$–$C_4$alkoxy, and $R_4$, $R_5$ and $R_6$, independently of one another, are hydrogen, $C_1$–$C_{12}$alkyl, $C_5$–$C_8$cycloalkyl, $C_1$–$C_4$alkoxy or unsubstituted or $C_1$–$C_4$alkyl-substituted phenyl.

Preference is also given to compositions in which $R_2$ is as defined for $R_1$, it being possible for $R_1$ and $R_2$ as

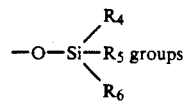

to be identical or different, or $R_2$ is $C_1$–$C_{12}$alkyl, phenyl-substituted $C_1$–$C_8$alkyl, $C_5$–$C_8$cycloalkyl, $C_6$–$C_{12}$aryl or $C_1$–$C_8$alkoxy, and, if $R_2$ is a

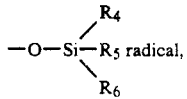

$R_6$ can link the silicon atoms to form a 7-membered ring, in which case

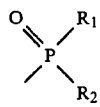

corresponds to the group IIa, $R_3$ is $C_1$-$C_{12}$alkyl, halogen-substituted $C_1$-$C_8$alkyl, unsubstituted or $C_1$-$C_8$alkyl-substituted $C_5$-$C_8$cycloalkyl, or unsubstituted or $C_1$-$C_8$alkyl-, $C_1$-$C_8$alkoxy- or halogen-substituted $C_6$-$C_{12}$aryl, and $R_4$, $R_5$ and $R_6$, independently of one another, are hydrogen, $C_1$-$C_{12}$alkyl, $C_5$-$C_8$cycloalkyl or unsubstituted or $C_1$-$C_4$alkyl-substituted phenyl.

A further preferred embodiment of the invention are compositions in which $R_2$ is as defined for $R_1$, it being possible for $R_1$ and $R_2$ as

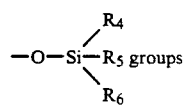

to be identical or different, or $R_2$ is phenyl, $C_1$-$C_4$alkoxy, unsubstituted or phenyl-substituted $C_1$-$C_4$alkyl, or, if $R_2$ is a

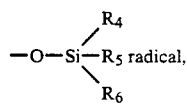

$R_6$ can link the silicon atoms to form a ring, in which case

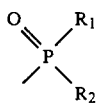

corresponds to the group IIa, $R_3$ is unsubstituted or halogen-substituted $C_1$-$C_4$alkyl, unsubstituted or $C_1$-$C_6$alkyl-, $C_1$-$C_4$alkoxy- or halogen-substituted phenyl, and $R_4$, $R_5$ and $R_6$, independently of one another, are hydrogen, $C_1$-$C_8$alkyl, $C_5$-$C_8$cycloalkyl or phenyl.

Preference is additionally given to compositions in which $R_2$ is as defined for $R_1$, it being possible for $R_1$ and $R_2$ as

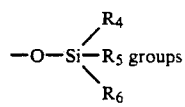

to be identical or different, or $R_2$ is phenyl, and, if $R_2$ is a

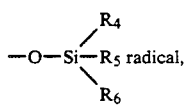

$R_6$ can link the silicon atoms to form a 7-membered ring, in which case

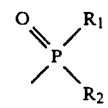

corresponds to the group IIa, $R_3$ is unsubstituted or halogen-substituted $C_1$-$C_4$alkyl or unsubstituted or $C_1$-$C_6$alkyl-, $C_1$-$C_4$alkoxy- or halogen-substituted phenyl, and $R_4$, $R_5$ and $R_6$, independently of one another, are $C_1$-$C_8$alkyl or phenyl.

The invention furthermore provides compositions which, in addition to the photoinitiator (b), contain at least one further photoinitiator and/or other additives.

The photopolymerisable compositions expediently contain the photoinitiator (b) in an amount of from 0.05 to 15% by weight, preferably from 0.2 to 5% by weight, based on the composition.

The invention also relates to compounds of the formula Ia

in which
$R_1$ is the

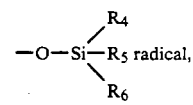

$R_2$ is as defined for $R_1$, it being possible for $R_1$ and $R_2$ as

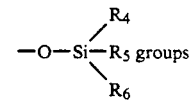

to be identical or different, or $R_2$ is $C_1$-$C_{18}$alkyl, phenyl-, $C_1$-$C_{12}$alkoxy- or halogen-substituted $C_1$-$C_8$alkyl, $C_2$-$C_{18}$alkenyl, unsubstituted or $C_1$-$C_{12}$alkyl-, $C_1$-$C_{12}$alkoxy-, phenyl- or halogen-substituted $C_5$-$C_8$cycloalkyl, unsubstituted or halogen-, $C_1$-$C_{12}$alkyl- or $C_1$-$C_{12}$alkoxy-substituted $C_6$-$C_{12}$aryl, an aromatic, O-, S- and/or N-containing 5- or 6-membered heterocyclic radical, which may be substituted by halogen, $C_1$-$C_4$alkyl or $C_1$-$C_4$alkoxy, or is $C_1$-$C_{12}$alkoxy, phenoxy or benzyloxy, and, if $R_2$ is a

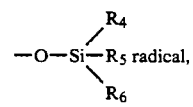

$R_6$ can link the silicon atoms to form 6-, 7- or 8-membered rings, in which case

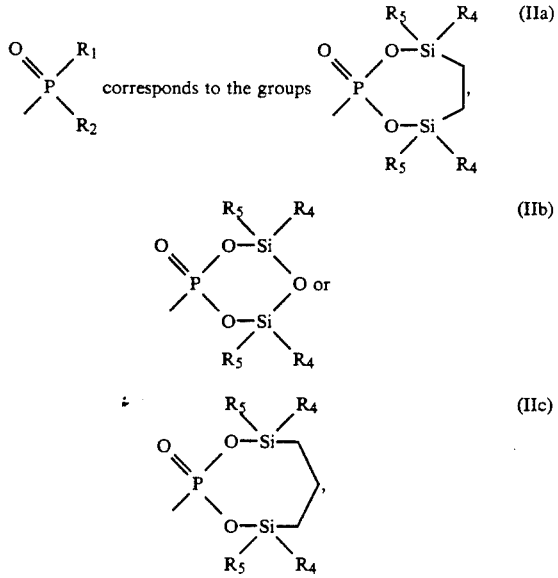 corresponds to the groups or $R_1$ and $R_2$, together with the —P=O group, can form a 4-membered ring of the formula

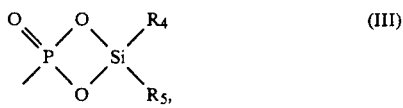

$R_3'$ is $C_1$-$C_{18}$alkyl, halogen-, phenyl- or $C_1$-$C_{12}$alkoxy-substituted $C_1$-$C_8$alkyl, $C_2$-$C_6$alkenyl, unsubstituted or $C_1$-$C_{12}$alkyl-, $C_1$-$C_{12}$alkoxy- or halogen-substituted $C_5$-$C_8$cycloalkyl, unsubstituted or $C_1$-$C_{12}$alkyl-, $C_1$-$C_{12}$alkoxy-, $C_2$-$C_{12}$alkoxyalkyl-, $C_1$-$C_4$alkylthio- or halogen-substituted $C_6$-$C_{12}$aryl, or a 5- or 6-membered, aromatic, O-, S- and/or N-containing heterocyclic radical, which may be substituted by halogen, $C_1$-$C_4$alkyl or $C_1$-$C_4$alkoxy, and $R_4$, $R_5$ and $R_6$, independently of one another, are hydrogen, $C_1$-$C_{18}$alkyl, $C_5$-$C_8$cycloalkyl, $C_1$-$C_{12}$alkoxy or unsubstituted or $C_1$-$C_8$alkyl-substituted phenyl, at least two of the radicals $R_4$, $R_5$ and $R_6$ being other than hydrogen, with the provisos that (1) if $R_1$ and $R_2$ are identical and $R_4$, $R_5$ and $R_6$ have the same meanings and are methyl or ethyl, $R_3'$ is not $C_1$-$C_5$alkyl, phenyl, methylphenyl, methoxyphenyl or halophenyl and (2) if $R_3'$ is methyl, $R_4$, $R_5$ and $R_6$ in the radical $R_1$ are not simultaneously ethyl.

Preference is given to compounds of the formula Ia in which $R_2$ is as defined for $R_1$, it being possible for $R_1$ and $R_2$ as

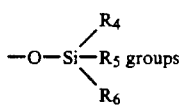

to be identical or different, or $R_2$ is $C_1$-$C_{12}$alkyl, phenyl-, $C_1$-$C_4$alkoxy- or halogen-substituted $C_1$-$C_8$alkyl, $C_2$-$C_8$alkenyl, unsubstituted or $C_1$-$C_4$alkyl-, $C_1$-$C_4$alkoxy-, phenyl- or halogen-substituted $C_5$-$C_8$cycloalkyl, unsubstituted or halogen-, $C_1$-$C_8$alkyl- or $C_1$-$C_4$alkoxy-substituted $C_6$-$C_{12}$aryl, or a 5- or 6-membered, aromatic, O-, S- and/or N-containing heterocyclic radical, which may be substituted by halogen, $C_1$-$C_4$alkyl or $C_1$-$C_4$alkoxy, or is $C_1$-$C_8$alkoxy, phenoxy or benzyloxy, and, if $R_2$ is a

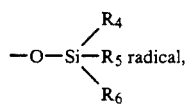 radical, $R_6$ can link the silicon atoms to form 6-, 7- or 8-membered rings, in which case

can correspond to the groups IIa, IIb or IIc, or $R_1$ and $R_2$, together with the —P=O group, can form a ring of the formula III, $R_3'$ is $C_1$-$C_{12}$alkyl, halogen-, $C_1$-$C_4$alkoxy- or phenyl-substituted $C_1$-$C_8$alkyl, $C_2$-$C_4$alkenyl, unsubstituted or $C_1$-$C_8$alkyl-, $C_1$-$C_4$alkoxy-or halogen-substituted $C_5$-$C_8$cycloalkyl, unsubstituted or $C_1$-$C_8$alkyl-, $C_1$-$C_8$alkoxy-, $C_2$-$C_8$alkoxyalkyl-, $C_1$-$C_4$alkylthio- or halogen-substituted $C_6$-$C_{12}$aryl, or a 5- or 6-membered, aromatic, O-, S- and/or N-containing heterocyclic radical, which may be substituted by halogen, $C_1$-$C_4$alkyl or $C_1$-$C_4$alkoxy, and $R_4$, $R_5$ and $R_6$, independently of one another, are hydrogen, $C_1$-$C_{12}$alkyl, $C_5$-$C_8$cycloalkyl, $C_1$-$C_4$alkoxy or unsubstituted or $C_1$-$C_4$alkyl-substituted phenyl.

Preference is also given to compounds of the formula Ia in which $R_2$ is as defined for $R_1$, it being possible for $R_1$ and $R_2$ as

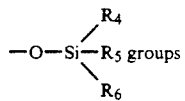

to be identical or different, or $R_2$ is $C_1$-$C_{12}$alkyl, phenyl-substituted $C_1$-$C_8$alkyl, $C_5$-$C_8$cycloalkyl, $C_6$-$C_{12}$aryl or $C_1$-$C_8$alkoxy, and, if $R_2$ is a

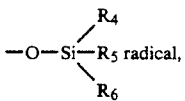 radical, $R_6$ can link the silicon atoms to form a 7-membered ring, in which case

corresponds to the group IIa, $R_3'$ is $C_1$-$C_{12}$alkyl, halogen-substituted $C_1$-$C_8$alkyl, unsubstituted or $C_1$-$C_8$alkyl-substituted $C_5$-$C_8$cycloalkyl, or unsubstituted or $C_1$-$C_8$alkyl-, $C_1$-$C_8$alkoxy-or halogen-substituted $C_6$-$C_{12}$aryl, and $R_4$, $R_5$ and $R_6$, independently of one another, are hydrogen, $C_1$-$C_{12}$alkyl, $C_5$-$C_8$cycloalkyl, $C_1$-$C_4$alkoxy or unsubstituted or $C_1$-$C_4$alkyl-substituted phenyl.

A further preferred embodiment are compounds of the formula Ia in which $R_2$ is as defined for $R_1$, it being possible for $R_1$ and $R_2$ as

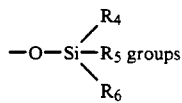 groups to be identical or different, or $R_2$ is unsubstituted or phenyl-substituted $C_1$–$C_4$alkyl, $C_1$–$C_4$alkoxy or phenyl, and, if $R_2$ is a

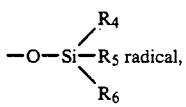 radical, $R_6$ can link the silicon atoms to form a 7-membered ring, in which case

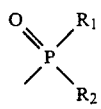

corresponds to the group IIa, $R_3'$ is unsubstituted or halogen-substituted $C_1$–$C_4$alkyl, unsubstituted or $C_1$–$C_6$alkyl-, $C_1$–$C_4$alkoxy- or halogen-substituted phenyl, and $R_4$, $R_5$ and $R_6$, independently of one another, are hydrogen, $C_1$–$C_8$alkyl or phenyl.

Preference is additionally given to compounds of the formula Ia in which $R_2$ is as defined for $R_1$, it being possible for $R_1$ and $R_2$ as

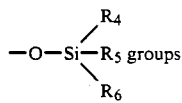 groups to be identical or different, or $R_2$ is phenyl, and, if $R_2$ is a

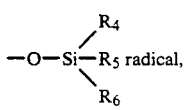 radical, $R_6$ can link the silicon atoms to form a 7-membered ring, in which case

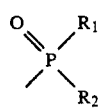

corresponds to the group IIa, $R_3'$ is halogen-substituted $C_1$–$C_4$alkyl or unsubstituted or $C_1$–$C_6$alkyl- or halogen-substituted phenyl, and $R_4$, $R_5$ and $R_6$, independently of one another, are $C_1$–$C_8$alkyl or phenyl.

Examples of individual compounds of the formula I are:
bis(trimethylsilyl) 2,4,6-trimethylbenzoylphosphonate
methyl-trimethylsilyl 2,6-dichlorobenzoylphosphonate
dimethyl tert-hexylsilyl 2,6-dimethoxybenzoylphenylphosphinate
diphenyl methylsilyl pivaloylisobutylphosphinate
ethyl cyclohexyldimethylsilyl 2,4,6-trimethylbenzoylphosphonate
trimethylsilyl 2,6-dimethoxybenzoylbenzylphosphinate
bis(diethylsilyl) 2-ethoxybenzoylphosphonate
bis(dimethylphenylsilyl) 2,2-bis(chloromethyl)propionylphosphonate.

The compounds of the formula I can be prepared by processes which are known per se, for example those described in the literature cited at the outset, in which the previously known compounds of the formula I are also disclosed.

The compounds of the formula I can be obtained, as described, for example, in THL (2), 155–8, 1977, from the corresponding alkyl esters of monoacylphosphine oxides by transesterification using trialkylchlorosilane:

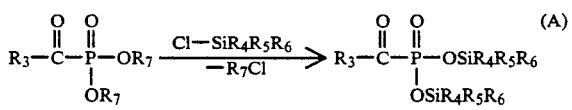 (A)

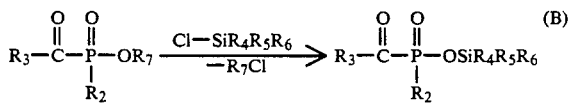 (B)

$R_7$ is alkyl or aryl. The other radicals are as defined above and in the claims. Depending on the stoichiometric ratio of the reactants, it is also possible to prepare the monosilyl monoalkyl ester compounds by (A). Furthermore, the trialkylchlorosilane may be replaced by trialkylbromosilane or trialkyliodosilane, as described, for example, in Synthesis (8), 609–12, 1978.

Another way of synthesising the compounds of the formula I is the Michaelis-Arbusov reaction in which an acid chloride is reacted with a tris(trialkylsilyl)phosphine, as described, for example, in EP-A-0 042 567:

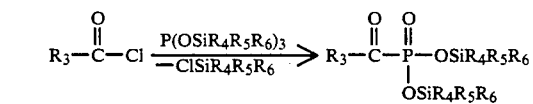

If the tris(trialkylsilyl)phosphine is replaced, for example, by a compound of the formula

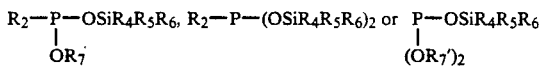

compounds such as 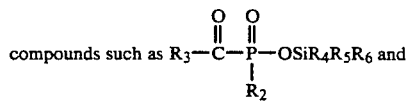 and

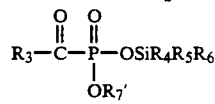

in which $R_7'$ is $C_1$–$C_{12}$alkyl, phenyl or benzyl, can be obtained. The compounds which contain cyclic structures of formulae IIa, IIb, IIc and III can also be prepared by the Michaelis-Arbusov reaction.

The preparation of the starting materials is known in general terms and is familiar to a person skilled in the art. The monoacylphosphine oxide starting materials in (A) and (B) can be prepared, for example, by Michaelis-Arbusov reaction of the corresponding phosphonites

[obtainable from the chlorophosphines by reaction with alcohols; cf. Houben-Weyl, Methoden d. Org. Chemie [Methods of Organic Chemistry], XII/1, 324–327 (1963), G. Thieme Verlag, Stuttgart] with acid chlorides. The synthesis of tris(trialkylsilyl)phosphines and their derivatives is also known in general terms and can be carried out, for example, by transesterification of P(OR)$_3$ using trialkylsilyl chloride [cf. J. Org. Chem. 28, 2975 (1963)].

The compounds of the formula I can be used according to the invention as photoinitiators for the photopolymerisation of ethylenically unsaturated compounds or mixtures which contain such compounds. Component (a) may be an ethylenically unsaturated, monomeric, oligomeric or polymeric compound which undergoes photopolymerisation to give relatively high-molecular-weight products and at the same time modifies its solubility.

The unsaturated compounds may contain one or more olefinic double bonds and may be of low molecular weight (monomeric) or relatively high molecular weight (oligomeric).

Examples of particularly suitable compounds are esters of ethylenically unsaturated carboxylic acids and polyols or polyepoxides, and polymers containing ethylenically unsaturated groups in the chain or in the side groups, for example unsaturated polyesters, polyamides and polyurethanes or copolymers thereof, polybutadiene and butadiene copolymers, polyisoprene and isoprene copolymers, polymers and copolymers containing (meth)acrylate groups in the side chains, and mixtures of one or more such polymers.

Examples of unsaturated carboxylic acids are acrylic acid, methacrylic acid, crotonic acid, itaconic acid, cinnamic acid and unsaturated fatty acids, such as linoleic acid and oleic acid. Acrylic acid and methacrylic acid are preferred.

Suitable polyols are aromatic and in particular aliphatic and cycloaliphatic polyols. Examples of aromatic polyols are hydroquinone, 4,4'-dihydroxydiphenyl, 2,2-di(4-hydroxyphenyl)propane, novolaks and resols. Examples of polyepoxides are those based on said polyols, in particular aromatic polyols and epichlorohydrin. Other suitable polyols are polymers and copolymers which contain hydroxyl groups in the polymer chain or in side groups, for example polyvinyl alcohol and copolymers thereof, or hydroxyalkyl polymethacrylates or copolymers thereof. Other suitable polyols are oligoesters containing hydroxyl end groups.

Examples of aliphatic and cycloaliphatic polyols are alkylenediols, preferably having 2 to 12 carbon atoms, such as ethylene glycol, 1,2- and 1,3-propanediol, 1,2-, 1,3- and 1,4-butanediol, pentanediol, hexanediol, octanediol, dodecanediol, diethylene glycol, triethylene glycol, polyethylene glycols having molecular weights of, preferably, from 200 to 1500, 1,3-cyclopentanediol, 1,2-, 1,3- and 1,4-cyclohexanediol, 1,4-dihydroxymethylcyclohexane, glycerol, tris($\beta$-hydroxyethyl)amine, trimethylolethane, trimethylolpropane, pentaerythritol, dipentaerythritol and sorbitol.

Polyols may be partially or fully esterified by means of one or more unsaturated carboxylic acids, where the free hydroxyl groups in partial esters may be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol having molecular weights of from 200 to 1500, or mixtures thereof.

Component (a) may also be a silylated resin, for example a polysiloxane containing acrylate functions.

Suitable compounds for component (a) are also the amides of identical or different unsaturated carboxylic acids of aromatic, cycloaliphatic and aliphatic polyamines, preferably having 2 to 6, in particular 2 to 4, amino groups. Examples of polyamines of this type are ethylenediamine, 1,2- and 1,3-propylenediamine, 1,2-, 1,3- and 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-$\beta$-aminoethyl ether, diethylenetriamine, triethylenetetramine, di($\beta$-aminoethoxy)ethane and di($\beta$-aminopropoxy)ethane. Other suitable polyamines are polymers and copolymers, possibly containing additional amino groups in the side chain, and oligoamides containing amino end groups. Examples of unsaturated amides of this type are: methylenebisacrylamide, 1,6-hexamethylenebisacrylamide, diethylenetriaminetrismethacrylamide, bis(methacrylamidopropoxy)ethane, $\beta$-methacrylamidoethyl methacrylate and N-[($\beta$-hydroxyethoxy)ethyl]acrylamide.

Suitable unsaturated polyesters and polyamides are derived, for example, from maleic acid and diols or diamines. Some of the maleic acid may be replaced by other dicarboxylic acids. They can be employed together with ethylenically unsaturated comonomers, for example styrene. The polyesters and polyamides can also be derived from dicarboxylic acids and ethylenically unsaturated diols or diamines, in particular from relatively long-chain compounds containing, for example, 6 to 20 carbon atoms. Examples of polyurethanes are those built up from saturated or unsaturated diisocyanates and unsaturated or saturated diols.

Polybutadiene and polyisoprene and copolymers thereof are known. Examples of suitable comonomers are olefins, such as ethylene, propene, butene, hexene, (meth)acrylates, acrylonitrile, styrene and vinyl chloride. Polymers containing (meth)acrylate groups in the side chain are also known. These may be, for example, products of the reaction of novolak-based epoxy resins with (meth)acrylic acid, homopolymers or copolymers of polyvinyl alcohol or hydroxyalkyl derivatives thereof which have been esterified using (meth)acrylic acid, or homopolymers or copolymers of (meth)acrylates which have been esterified using hydroxyalkyl (meth)acrylates.

The photopolymerisable compounds may be employed alone or in any desired mixtures. Preference is given to mixtures of polyol (meth)acrylates.

It is also possible to add binders to the compositions according to the invention; this is particularly expedient if the photopolymerisable compounds are liquid or viscous substances. The amount of binder may be, for example, from 5 to 95% by weight, preferably from 10 to 90% by weight and in particular from 50 to 90% by weight, based on the total composition. The binder is chosen depending on the area of application and on the properties required thereof, such as developing ability in aqueous and organic solvent systems, adhesion to substrates and oxygen sensitivity.

Examples of suitable binders are polymers having a molecular weight of from about 5000 to 2,000,000, preferably 10,000 to 1,000,000. Examples are: homopolymeric and copolymeric acrylates and methacrylates, for example copolymers of methyl methacrylate/ethyl acrylate/methacrylic acid, poly(alkyl methacrylates), poly(alkyl acrylates); cellulose esters and ethers, such as cellulose acetate, cellulose acetate butyrate, methylcellulose and ethylcellulose; polyvinylbutyral, polyvinylformal, cyclised rubber, polyethers, such as polyethylene oxide, polypropylene oxide and polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), and polyesters, such as poly(ethylene glycol terephthalate) and poly(hexamethylene glycol succinate).

The unsaturated compounds may also be used in mixtures with non-photopolymerisable, film-forming components. These may be, for example, physically drying polymers or solutions thereof in organic solvents, for example nitrocellulose or cellulose acetobutyrate. However, they may also be chemically or thermally curable resins, for example polyisocyanates, polyepoxides or melamine resin. The additional use of thermocurable resins is important for use in so-called hybrid systems, which are photopolymerised in a first step and crosslinked by thermal aftertreatment in a second step.

The photopolymerisable mixtures may contain various additives in addition to the photoinitiator. Examples are thermal inhibitors, which are intended to prevent premature polymerisation, in particular during the preparation of the compositions by mixing the components, for example hydroquinone, hydroquinone derivatives, p-methoxyphenol, β-naphthol or sterically hindered phenols, for example 2,6-di(tert-butyl)-p-cresol. The shelf life in the dark can be increased by using, for example, copper compounds, such as copper naphthenate, stearate or octanoate, phosphorus compounds, for example triphenylphosphine, tributylphosphine, triethyl phosphite, triphenyl phosphite or tribenzyl phosphite, quaternary ammonium compounds, for example trimethylammonium chloride or trimethylbenzylammonium chloride, or hydroxylamine derivatives, for example N-diethylhydroxylamine.

In order to exclude atmospheric oxygen during the polymerisation, paraffin or similar wax-like substances can be added; these migrate to the surface on commencement of the polymerisation due to low solubility in the polymer and form a transparent surface layer which prevents contact with air.

Light stabilisers which can be added in small amounts are UV absorbers, for example those of the benzotriazole, benzophenone or oxalanilide type. It is also possible to add light stabilisers of sterically hindered amine type (HALS).

In certain cases, it may be advantageous to use mixtures of two or more of the photoinitiators according to the invention. It is of course also possible to use mixtures with known photoinitiators, for example mixtures with initiators of the benzophenone type, acetophenone derivative type, for example α-hydroxycycloalkyl phenyl ketones, α-aminoketones, benzoin alkyl ethers and benzil ketals, or of the unsilylated acylphosphine oxide or titanocene type.

The photopolymerisation can be accelerated, in particular in pigmented preparations, by adding amines, for example triethanolamine, N-methyldiethanolamine, ethyl p-dimethylaminobenzoate or Michler's ketone. The effect of the amines can be increased by adding aromatic ketones of the benzophenone type.

The photopolymerisation can also be accelerated by adding photosensitisers, which shift or broaden the spectral sensitivity. These are, in particular, aromatic carbonyl compounds, for example derivatives of benzophenone, thioxanthone, anthraquinone or 3-acylcoumarine, and 3-(aroylmethylene)thiazolines.

Examples of other conventional additives - depending on the intended use - are fillers, pigments, dyes, adhesives, wetting agents and flow assitants.

The photopolymerisable compositions can be used for various purposes, for example as printing inks, varnishes, white paints, surface coatings, coatings for exterior use, for photographic reproduction processes, for image recording processes and for the production of printing plates, as dental filling materials, as adhesives, as coatings for optical fibres, for printed circuits and for coating electronic components.

In surface coatings, two-component mixtures of a prepolymer with a polyunsaturated monomer, or three-component mixtures which additionally contain a monounsaturated monomer are frequently used. The prepolymer here is primarily responsible for the properties of the coating film, and variation thereof allows a person skilled in the art to modify the properties of the cured film. The polyunsaturated monomer functions as a crosslinking agent which renders the coating film insoluble. The monounsaturated monomer functions as a reactive thinner by means of which the viscosity is reduced without the need to use a solvent.

Two- and three-component systems based on a prepolymer are used for printing inks and for surface coatings, photoresists and other photocurable compositions. The binders used for printing inks are frequently also single-component systems based on photocurable prepolymers.

Unsaturated polyester resins are usually used in two-component systems together with a monounsaturated monomer, preferably styrene. For photoresists, specific one-component systems are frequently used, for example polymaleimides, polychalcones or polyimides, as described in DE-A 2 308 830.

The photocurable compositions according to the invention are suitable as coating compositions for substrates of all types, for example wood, paper, ceramics, plastics, such as polyesters and cellulose acetate films, and metals, such as copper and aluminium, onto which a protective coating or an image can be applied by photopolymerisation.

The coating of the substrates can be carried out by applying a liquid composition, a solution or suspension to the substrate. This is effected, for example, by dipping, brushing, spraying or reverse roll coating. The application rate (coating thickness) and the substrate type (coating base) depend on the desired area of application. Coating bases for photographic information recording are, for example, films made of polyester, cellulose acetate or plastic-coated paper; bases for offset printing plates are specially treated aluminium, and bases for the production of printed circuits are copper-coated laminates. The coating thicknesses for photographic materials and offset printing plates are generally from about 0.5 to about 10 $\mu$m. If solvents are additionally used, they are removed after the coating operation.

Photocuring has considerable importance for printing inks since the drying time of the binder is a crucial factor for the production rate of graphic products and should be in the order of fractions of seconds. UV-curable printing inks are important, in particular, for screen printing.

The photocurable mixtures according to the invention are also highly suitable for the production of printing plates, where, for example, mixtures of soluble, linear polyamides or styrene-butadiene rubber with photopolymerisable monomers, for example acrylamides, and a photoinitiator are used. Films and plates made from these systems (wet or dry) are exposed through the negative (or positive) of the print master, and the uncured areas are subsequently removed using a solvent.

A further area of application for photocuring is metal coating, for example in the coating of metal sheeting and tubes, cans or bottle caps, and the photocuring of plastic coatings, for example PVC-based floor or wall coverings.

Examples of the photocuring of paper coatings are the colourless coating of labels, record sleeves or book covers.

The use of photocurable compositions for imaging processes and for the optical production of information carriers is also important. Here, the coating (wet or dry) applied to the base is irradiated with short-wave light through a photomask, and the unexposed areas of the coating are removed by treatment with a solvent (=developer). The photocurable coating can also be applied to metal by electrodeposition. The exposed areas are crosslinked and polymeric and are therefore insoluble and remain on the base. Appropriate staining gives visible images. If the base is a metallised layer, the metal can be removed in the unexposed areas by etching after exposure and development or increased in thickness by electroplating. In this way, printed circuits and photoresists can be produced.

The invention also relates to a process for the photopolymerisation of nonvolatile, monomeric, oligomeric or polymeric compounds containing at least one ethylenically unsaturated double bond, which comprises adding a compound of the formula I to the above-mentioned compounds and irradiating the mixture with light in the range from 200 to 600 nm.

The polymerisation is carried out by known methods of photopolymerisation by irradiation with sunlight or with light which contains a high proportion of short-wave radiation. Examples of suitable light sources are mercury medium-pressure, high-pressure and low-pressure lamps, superactinic fluorescent tubes, metal halide lamps or lasers, whose emission maxima are in the range between 250 and 450 nm. Laser light sources have the advantage that photomasks are unnecessary since the controlled laser beam writes directly onto the photocurable layer. In the case of a combination with photosensitisers, relatively long-wave light or laser beams up to 600 nm can also be used.

The compositions are prepared by mixing the individual components.

The invention furthermore relates to a cured composition obtained by the above-described process.

The compounds according to the invention have good solubility in the resins usually used. The solubility in and compatibility with silylated resins, i.e. polysiloxanes containing acrylate functions, should also be emphasised. The compositions containing compounds of the formula I have good shelf lives. Incorporation of the compounds of the formula I into surface coatings results in low-odour, yellowing-resistant coatings.

The examples below illustrate the invention in greater detail. Parts and percentages are by weight, unless stated otherwise, in the remainder of the description and the patent claims.

EXAMPLE 1

Preparation of

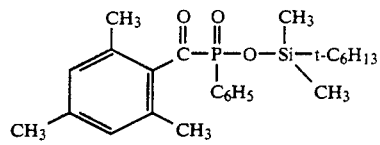

t-C$_6$H$_{13}$ is 1,1,2,2-tetramethylethyl.

6.0 g (0.02 mol) of methyl 2,4,6-trimethylbenzoyl-phenylphosphinate and 4.3 g (0.024 mol) of tert-hexyl-dimethylchlorosilane are warmed to 160° C. with stirring and stirred at this temperature for a further 3 hours, the methyl chloride formed being collected in a cold trap. The mixture is cooled, and the residue is distilled in a high-vacuum bulb tube (boiling point 170° C./0.1 mbar), giving 5.9 g (68.8% of theory) of the title compound as a clear, yellowish oil.

| Elemental analysis: | calc.: C 66.94% H 8.19% |
|---|---|
|  | found: C 66.62% H 8.20% |

EXAMPLES 2-7

The compounds of the examples 2-7 are prepared analogously to the compound of example 1. The structures and physical data are shown in Table 1.

TABLE 1

| Example | Structure | Physical properties | Elemental analysis [%] calc. / found | | | |
|---|---|---|---|---|---|---|
| | | | C | H | P | Cl |
| 1 | 2,4,6-trimethylphenyl-C(O)-P(O)(C6H5)-O-Si(CH3)2-t-C6H13 | b.p. 170° C./ 0.1 mbar | 66.94 / 66.62 | 8.19 / 8.20 | | |
| 2 | C6H5-C(O)-P(O)-[O-Si(CH3)3]2 | b.p. 150° C./ 0.13 mbar | 47.25 / 47.14 | 7.02 / 6.97 | 9.37 / 9.87 | |
| 3 | 2,4,6-trimethylphenyl-C(O)-P(O)-[O-Si(CH3)3]2 | b.p. 190° C./ 0.13 mbar | 51.58 / 51.37 | 7.85 / 7.82 | 8.31 / 9.00 | |
| 4 | 2-chlorophenyl-C(O)-P(O)-[O-Si(CH3)3]2 | b.p. 160° C./ 0.13 mbar | 42.79 / 42.92 | 6.08 / 6.24 | 8.49 / 8.76 | 9.72 / 9.72 |
| 5 | 2,4,6-trimethylphenyl-C(O)-P(O)(C6H5)-O-Si(CH3)2-t-C4H9 | b.p. 190° C./ 0.8 mbar | 65.64 / 65.19 | 7.76 / 7.69 | | |
| 6 | 2,4,6-trimethylphenyl-C(O)-P(O)(C6H5)-O-Si(C6H5)3 | b.p. 240° C./ 1.5 mbar | 74.70 / 74.73 | 5.72 / 5.88 | | |
| 7 | 2,4,6-trimethylphenyl-C(O)-P(O)[O-Si(CH3)2-CH2-CH2-Si(CH3)2-O] (cyclic) | b.p. 190° C./ 2.0 mbar | 51.86 / 49.30 | 7.35 / 7.34 | | |

EXAMPLE 8

Preparation of

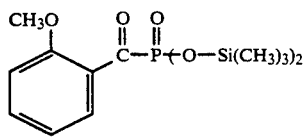

8.7 g (0.029 mol) of tris(trimethylsilyl) phosphite are added dropwise at 80° C. under nitrogen over the course of 20 minutes to a solution of 4.8 g (0.028 mol) of 2-methoxybenzoyl chloride in 100 ml of toluene. The mixture is stirred at 80° C. for 3 hours, and the yellowish solution is allowed to cool to room temperature and evaporated on a rotary evaporator. The residue is purified by distillation, giving 4.0 g (40% of theory) of the title compound as a pale yellow oil having a boiling point of 118° C./2 mbar.

| Elemental analysis: | calc.: C 46.65% H 6.99% |
|---|---|
| | found: C 46.42% H 7.40% |

EXAMPLES 9-11

The compounds of Examples 9-11 are prepared analogously to the compound of Example 8 using the appropriate acid chlorides. The compounds and the elemental analyses of the oils are shown in Table 2 below.

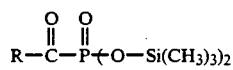

TABLE 2

| Example | R | Elemental analysis [%] | | |
|---|---|---|---|---|
| | | C | H | calculated found |
| 9 | CH₃O—⟨phenyl⟩— | 46.65<br>46.22 | 6.99<br>6.81 | |
| 10 | H₃C—C(CH₂—Cl)₂— | 74.83<br>74.65 | 6.64<br>6.64 | |
| 11 | t-butyl | 42.55<br>42.25 | 8.77<br>9.15 | |

EXAMPLE 12

Initiator reactivity in a varnish

A photopolymerisable composition is prepared from 99.5 parts of ®Roskydal UV 502 A (solution of an unsaturated polyester in styrene; BAYER, Germany) 0.5 part of ®BYK 300 (flow assistant; Byk-Mallinckrodt)

2% by weight of the photoinitiator to be tested are mixed with this composition. The formulation is applied in a coating thickness of 100 μm to chipboard coated with white synthetic resin. The samples are then irradiated in a PPG irradiator with mercury medium-pressure lamps (2×80 W/cm). During this operation, the sample is passed, on a belt running at a speed of 20 m/min, under the lamps sufficiently frequently to give a wipe-resistant coating surface. The lower the number of passes, the better the photoinitiator action of the compound tested. The hardness of the sample is determined by measuring the König pendulum hardness (DIN 53 157). The larger the number of seconds, the harder the sample tested. The yellowing of the sample is measured as the yellowness index in accordance with ASTM D 1925-70, once immediately after exposure and once after exposure for a further 4 hours. The lower the value, the lower the yellowing of the sample.

The results are shown in Table 3.

TABLE 3

| Compound from Example No. | Wipe resistance [number of passes at 20 m/min] | Pendulum hardness [s] | Yellowness Index immediately | Yellowness Index after 4h |
|---|---|---|---|---|
| 1 | 3 | 139 | 9.2 | 6.9 |
| 3 | 6 | 97 | 7.3 | 7.0 |
| 5 | 4 | 135 | 8.3 | 7.1 |
| 6 | 5 | 139 | 8.0 | 7.4 |
| 7 | 7 | — | 7.0 | 7.0 |

What is claimed is:

1. A photopolymerisable composition comprising
(a) at least one ethylenically unsaturated, photopolymerisable compound and
(b) as photoinitiator at least one compound of the formula I $$R_3-C(=O)-P(=O)(R_1)(R_2) \quad (I)$$

in which $R_1$ is the $$-O-Si(R_4)(R_5)(R_6) \text{ radical,}$$

$R_2$ is as defined for $R_1$, it being possible for $R_1$ and $R_2$ as $$-O-Si(R_4)(R_5)(R_6) \text{ groups}$$

to be identical or different, or $R_2$ is $C_1$-$C_{18}$alkyl, phenyl-, $C_1$-$C_{12}$alkoxy- or halogen-substituted $C_1$-$C_8$alkyl, $C_2$-$C_{18}$alkenyl, unsubstituted or $C_1$-$C_{12}$alkyl-, $C_1$-$C_{12}$alkoxy-, phenyl- or halogen-substituted $C_5$-$C_8$cycloalkyl, unsubstituted or halogen-, $C_1$-$C_{12}$alkyl- or $C_1$-$C_{12}$alkoxy-substituted $C_6$-$C_{12}$aryl, an aromatic, O-, S- and/or N-containing 5- or 6-membered heterocyclic radical, which may be substituted by halogen, $C_1$-$C_4$alkyl or $C_1$-$C_4$alkoxy, or is $C_1$-$C_{12}$alkoxy, phenoxy or benzyloxy, and, if $R_2$ is a $$-O-Si(R_4)(R_5)(R_6) \text{ radical,}$$

$R_6$ can link the silicon atoms to form 6-, 7- or 8-membered rings, in which case

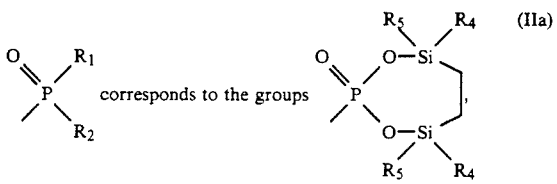

corresponds to the groups (IIa)

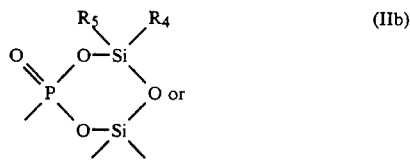

(IIb)

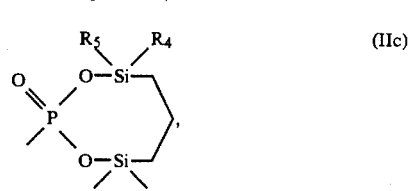

(IIc)

or $R_1$ and $R_2$, together with the —P=O group, can form a 4-membered ring of the formula

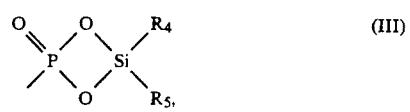

(III)

$R_3$ is $C_1$-$C_{18}$alkyl, halogen-, phenyl- or $C_1$-$C_{12}$alkoxy-substituted $C_1$-$C_8$alkyl, $C_2$-$C_6$alkenyl, unsubstituted or $C_1$-$C_{12}$alkyl-, $C_1$-$C_{12}$alkoxy- or halogen-substituted $C_5$-$C_8$cycloalkyl, unsubstituted or $C_1$-$C_{12}$alkyl-, $C_1$-$C_{12}$alkoxy-, $C_2$-$C_{12}$alkoxyalkyl-, $C_1$-$C_4$alkylthio- or halogen-substituted $C_6$-$C_{12}$aryl, or a 5- or 6-membered, aromatic, O-, S- and/or N-containing heterocyclic radical, which may be substituted by halogen, $C_1$-$C_4$alkyl or $C_1$-$C_4$alkoxy, and $R_4$, $R_5$ and $R_6$, independently of one another, are hydrogen, $C_1$-$C_{18}$alkyl, $C_5$-$C_8$cycloalkyl, $C_1$-$C_{12}$alkoxy or unsubstituted or $C_1$-$C_8$alkyl-substituted phenyl, at least two of the radicals $R_4$, $R_5$ and $R_6$ being other than hydrogen.

2. A composition according to claim 1, in which $R_2$ is as defined for $R_1$, it being possible for $R_1$ and $R_2$ as

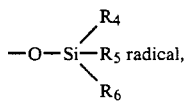 groups to be identical or different, or $R_2$ is $C_1$-$C_{12}$alkyl, phenyl-, $C_1$-$C_4$alkoxy- or halogen-substituted $C_1$-$C_8$alkyl, $C_2$-$C_8$alkenyl, unsubstituted or $C_1$-$C_4$alkyl-, $C_1$-$C_4$alkoxy-, phenyl- or halogen-substituted $C_5$-$C_8$cycloalkyl, unsubstituted or halogen-, $C_1$-$C_8$alkyl- or $C_1$-$C_4$alkoxy-substituted $C_6$-$C_{12}$aryl, or a 5- or 6-membered, aromatic, O-, S- and/or N-containing heterocyclic radical, which may be substituted by halogen, $C_1$-$C_4$alkyl or $C_1$-$C_4$alkoxy, or is $C_1$-$C_8$alkoxy, phenoxy or benzyloxy, and, if $R_2$ is a

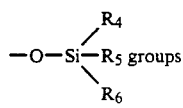 radical, $R_6$ can link the silicon atoms to form 6-, 7- or 8-membered rings, in which case

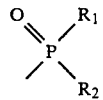

can correspond to the groups IIa, IIb or IIc, or $R_1$ and $R_2$, together with the —P=O group, can form a ring of the formula III, $R_3$ is $C_1$-$C_{12}$alkyl, halogen-, $C_1$-$C_4$alkoxy- or phenyl-substituted $C_1$-$C_8$alkyl, $C_2$-$C_4$alkenyl, unsubstituted or $C_1$-$C_8$alkyl-, $C_1$-$C_4$alkoxy- or halogen-substituted $C_5$-$C_8$cycloalkyl, unsubstituted or $C_1$-$C_8$alkyl-, $C_1$-$C_8$alkoxy-, $C_2$-$C_8$alkoxyalkyl-, $C_1$-$C_4$alkylthio- or halogen-substituted $C_6$-$C_{12}$aryl, or a 5- or 6-membered, aromatic, O-, S- and/or N-containing heterocyclic radical, which may be substituted by halogen, $C_1$-$C_4$alkyl or $C_1$-$C_4$alkoxy, and $R_4$, $R_5$ and $R_6$, independently of one another, are hydrogen $C_1$-$C_{12}$alkyl, $C_5$-$C_8$cycloalkyl, $C_1$-$C_4$alkoxy or unsubstituted or $C_1$-$C_4$alkyl-substituted phenyl.

3. A composition according to claim 2, in which $R_2$ is as defined for $R_1$, it being possible for $R_1$ and $R_2$ as

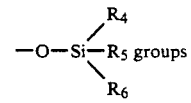 groups to be identical or different, or $R_2$ is $C_1$-$C_{12}$alkyl, phenyl-substituted $C_1$-$C_8$alkyl, $C_5$-$C_8$cycloalkyl, $C_6$-$C_{12}$aryl or $C_1$-$C_8$alkoxy, and, if $R_2$ is a

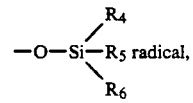 radical, $R_6$ can link the silicon atoms to form a 7-membered ring, in which case

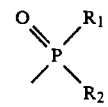

corresponds to the group IIa, $R_3$ is $C_1$-$C_{12}$alkyl, halogen-substituted $C_1$-$C_8$alkyl, unsubstituted or $C_1$-$C_8$alkyl-substituted $C_5$-$C_8$cycloalkyl, or unsubstituted or $C_1$-$C_8$alkyl-, $C_1$-$C_8$alkoxy- or halogen-substituted $C_6$-$C_{12}$aryl, and $R_4$, $R_5$ and $R_6$, independently of one another, are hydrogen, $C_1$-$C_{12}$alkyl, $C_5$-$C_8$cycloalkyl or unsubstituted or $C_1$-$C_4$alkyl-substituted phenyl.

4. A composition according to claim 3, in which $R_2$ is as defined for $R_1$, it being possible for $R_1$ and $R_2$ as

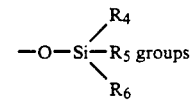 groups to be identical or different, or $R_2$ is phenyl, $C_1$-$C_4$alkoxy, unsubstituted or phenyl-substituted $C_1$-$C_4$alkyl, or, if $R_2$ is a

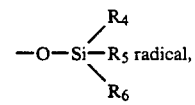 radical, $R_6$ can link the silicon atoms to form a ring, in which case

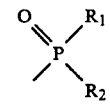

corresponds to the group IIa, $R_3$ is unsubstituted or halogen-substituted $C_1$-$C_4$alkyl, unsubstituted or $C_1$-$C_6$alkyl-, $C_1$-$C_4$alkoxy- or halogen-substituted phenyl, and $R_4$, $R_5$ and $R_6$, independently of one another, are hydrogen, $C_1$-$C_8$alkyl, $C_5$-$C_8$cycloalkyl or phenyl.

5. A composition according to claim 4, in which $R_2$ is as defined for $R_1$, it being possible for $R_1$ and $R_2$ as

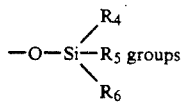 groups to be identical or different, or $R_2$ is phenyl, and, if $R_2$ is a

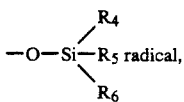 radical, $R_6$ can link the silicon atoms to form a 7-membered ring, in which case

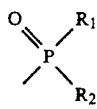

corresponds to the group IIa, $R_3$ is unsubstituted or halogen-substituted $C_1$–$C_4$alkyl or unsubstituted or $C_1$–$C_6$alkyl-, $C_1$–$C_4$alkoxy- or halogen-substituted phenyl, and $R_4$, $R_5$ and $R_6$, independently of one another, are $C_1$–$C_8$alkyl or phenyl.

6. A composition according to claim 1, which comprises, in addition to the photoinitiator (b), at least one further photoinitiator and/or other additives.

7. A composition according to claim 1, comprising from 0.05 to 15% by weight of component (b), based on the composition.

8. A composition according to claim 7, comprising from 0.2 to 5% by weight of component (b), based on the composition.

9. A compound of the formula Ia

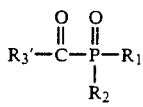 (Ia)

in which
$R_1$ is the

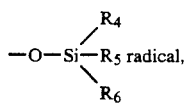 radical, $R_2$ is as defined for $R_1$, it being possible for $R_1$ and $R_2$ as

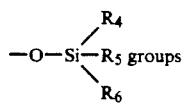 groups to be identical or different, or $R_2$ is $C_1$–$C_{18}$alkyl, phenyl-, $C_1$–$C_{12}$alkoxy- or halogen-substituted $C_1$–$C_8$alkyl, $C_2$–$C_{18}$alkenyl, unsubstituted or $C_1$–$C_{12}$alkyl-, $C_1$–$C_{12}$alkoxy-, phenyl- or halogen-substituted $C_5$–$C_8$cycloalkyl, unsubstituted or halogen-, $C_1$–$C_{12}$alkyl- or $C_1$–$C_{12}$alkoxy-substituted $C_6$–$C_{12}$aryl, an aromatic, O-, S- and/or N-containing 5- or 6-membered heterocyclic radical, which may be substituted by halogen, $C_1$–$C_4$alkyl or $C_1$–$C_4$alkoxy, or is $C_1$–$C_{12}$alkoxy, phenoxy or benzyloxy, and, if $R_2$ is a

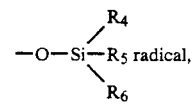 radical, $R_6$ can link the silicon atoms to form 6-, 7- or 8-membered rings, in which case

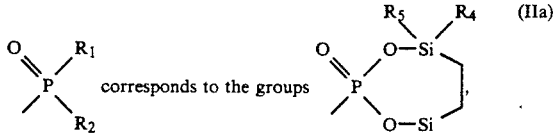 corresponds to the groups

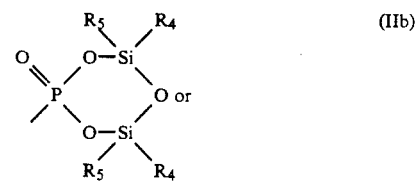

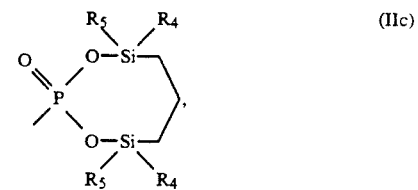

or $R_1$ and $R_2$, together with the —P=O group, can form a 4-membered ring of the formula

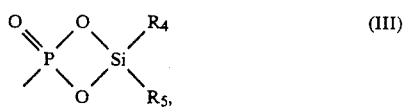

$R_3{}'$ is $C_1$–$C_{18}$alkyl, halogen-, phenyl- or or $C_1$–$C_{12}$alkoxy-substituted $C_1$–$C_8$alkyl, $C_2$–$C_6$alkenyl, unsubstituted or $C_1$–$C_{12}$alkyl-, $C_1$–$C_{12}$alkoxy- or halogen-substituted $C_5$–$C_8$cycloalkyl, unsubstituted or $C_1$–$C_{12}$alkyl-, $C_1$–$C_{12}$alkoxy-, $C_2$–$C_{12}$alkoxyalkyl-, $C_1$–$C_4$alkylthio- or halogen-substituted $C_6$–$C_{12}$aryl, or a 5- or 6-membered, aromatic, O-, S- and/or N-containing heterocyclic radical, which may be substituted by halogen, $C_1$–$C_4$alkyl or $C_1$–$C_4$alkoxy, and $R_4$, $R_5$ and $R_5$, independently of one another, are hydrogen, $C_1$–$C_{18}$alkyl, $C_5$–$C_8$cycloalkyl, $C_1$–$C_{12}$alkoxy or unsubstituted or $C_1$–$C_8$alkyl-substituted phenyl, at least two of the radicals $R_4$, $R_5$ and $R_6$ being other than hydrogen, with the provisos that (1) if $R_1$ and $R_2$ are identical and $R_4$, $R_5$ and $R_6$ have the same meanings and are methyl or ethyl, $R_3{}'$ is not $C_1$–$C_5$alkyl, phenyl, methylphenyl, methoxyphenyl or halophenyl and (2) if $R_3{}'$ is methyl, $R_4$, $R_5$ and $R_6$ in the radical $R_1$ are not simultaneously ethyl.

10. A compound according to claim 9, in which $R_2$ is as defined for $R_1$, it being possible for $R_1$ and $R_2$ as

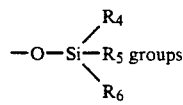

to be identical or different, or $R_2$ is $C_1$-$C_{12}$alkyl, phenyl-, $C_1$-$C_4$alkoxy- or halogen-substituted $C_1$-$C_8$alkyl, $C_2$-$C_8$alkenyl, unsubstituted or $C_1$-$C_4$alkyl-, $C_1$-$C_4$alkoxy-, phenyl- or halogen-substituted $C_5$-$C_8$cycloalkyl, unsubstituted or halogen-, $C_1$-$C_8$alkyl- or $C_1$-$C_4$alkoxy-substituted $C_6$-$C_{12}$aryl, or a 5- or 6-membered, aromatic, O-, S- and/or N-containing heterocyclic radical, which may be substituted by halogen, $C_1$-$C_4$alkyl or $C_1$-$C_4$alkoxy, or is $C_1$-$C_8$alkoxy, phenoxy or benzyloxy, and, if $R_2$ is a

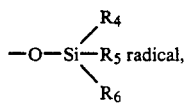

$R_6$ can link the silicon atoms to form 6-, 7- or 8-membered rings, in which case

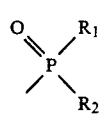

can correspond to the groups IIa, IIb or IIc, or $R_1$ and $R_2$, together with the —P=O group, can form a ring of the formula III, $R_3'$ is $C_1$-$C_{12}$alkyl, halogen-, $C_1$-$C_4$alkoxy- or phenyl-substituted $C_1$-$C_8$alkyl, $C_2$-$C_4$alkenyl, unsubstituted or $C_1$-$C_8$alkyl-, $C_1$-$C_4$alkoxy- or halogen-substituted $C_5$-$C_8$cycloalkyl, unsubstituted or $C_1$-$C_8$alkyl-, $C_1$-$C_8$alkoxy-, $C_2$-$C_8$alkoxyalkyl-, $C_1$-$C_4$alkylthio- or halogen-substituted $C_6$-$C_{12}$aryl, or a 5- or 6-membered, aromatic, O-, S- and/or N-containing heterocyclic radical, which may be substituted by halogen, $C_1$-$C_4$alkyl or $C_1$-$C_4$alkoxy, and $R_4$, $R_5$ and $R_6$, independently of one another, are hydrogen, $C_1$-$C_{12}$alkyl, $C_5$-$C_8$cycloalkyl, $C_1$-$C_4$alkoxy or unsubstituted or $C_1$-$C_4$alkyl-substituted phenyl.

11. A compound according to claim 9, in which $R_2$ is as defined for $R_1$, it being possible for $R_1$ and $R_2$ as

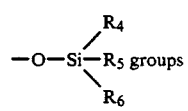

to be identical or different, or $R_2$ is $C_1$-$C_{12}$alkyl, phenyl-substituted $C_1$-$C_8$alkyl, $C_5$-$C_8$cycloalkyl, $C_6$-$C_{12}$aryl or $C_1$-$C_8$alkoxy, and, if $R_2$ is a

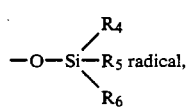

$R_6$ can link the silicon atoms to form a 7-membered ring, in which case

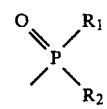

corresponds to the group IIa, $R_3'$ is $C_1$-$C_{12}$alkyl, halogen-substituted $C_1$-$C_8$alkyl, unsubstituted or $C_1$-$C_8$alkyl-substituted $C_5$-$C_8$cycloalkyl, or unsubstituted or $C_1$-$C_8$alkyl-, $C_1$-$C_8$alkoxy- or halogen-substituted $C_6$-$C_{12}$aryl, and $R_4$, $R_5$ and $R_6$, independently of one another, are hydrogen, $C_1$-$C_{12}$alkyl, $C_5$-$C_8$cycloalkyl, $C_1$-$C_4$alkoxy or unsubstituted or $C_1$-$C_4$alkyl-substituted phenyl.

12. A compound according to claim 11, in which $R_2$ is as defined for $R_1$, it being possible for $R_1$ and $R_2$ as

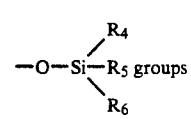

to be identical or different, or $R_2$ is unsubstituted or phenyl-substituted $C_1$-$C_4$alkyl, $C_1$-$C_4$alkoxy or phenyl, and, if $R_2$ is a

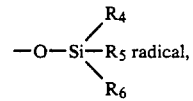

$R_6$ can link the silicon atoms to form a 7-membered ring, in which case

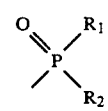

corresponds to the group IIa, $R_3'$ is unsubstituted or halogen-substituted $C_1$-$C_4$alkyl, unsubstituted or $C_1$-$C_6$alkyl-, $C_1$-$C_4$alkoxy- or halogen-substituted phenyl, and $R_4$, $R_5$ and $R_6$, independently of one another, are hydrogen, $C_1$-$C_8$alkyl or phenyl.

13. A compound according to claim 12, in which $R_2$ is as defined for $R_1$, it being possible for $R_1$ and $R_2$ as

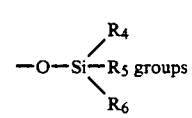

to be identical or different, or $R_2$ is phenyl, and, if $R_2$ is a

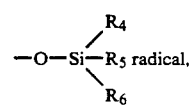

$R_6$ can link the silicon atoms to form a 7-membered ring, in which case

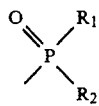

corresponds to the group IIa, $R_3'$ is halogen-substituted $C_1$–$C_4$alkyl or unsubstituted or $C_1$–$C_6$alkyl- or halogen-substituted phenyl, and $R_4$, $R_5$ and $R_6$, independently of one another, are $C_1$–$C_8$alkyl or phenyl.

14. A process for the photopolymerisation of compounds containing ethylenically unsaturated double bonds, which comprises irradiating a composition according to claim 1 with light in the range from 200 to 600 nm.

15. A cured composition obtained by a process according to claim 14.

* * * * *